(12) United States Patent
Okamoto et al.

(10) Patent No.: US 7,229,540 B2
(45) Date of Patent: Jun. 12, 2007

(54) BIOCHIP AND A MANUFACTURING METHOD OF BIOCHIP

(75) Inventors: Naomichi Okamoto, Hamamatsu (JP); Noriyuki Okumiya, Hamamatsu (JP); Ryo Sugimura, Hamamatsu (JP)

(73) Assignees: President of Shizuoka University, a Japanese Government Agency, Shizuoka-shi, Shizuoka (JP); ASTI Corporation, Hamamatsu-shi, Shizuoka (JP)

( * ) Notice: Subject to any disclaimer, the term of this patent is extended or adjusted under 35 U.S.C. 154(b) by 595 days.

(21) Appl. No.: 10/337,352

(22) Filed: Jan. 7, 2003

(65) Prior Publication Data

US 2004/0084311 A1 May 6, 2004

(30) Foreign Application Priority Data

Nov. 1, 2002 (JP) ............................. 2002-319211

(51) Int. Cl.
- *G01N 27/447* (2006.01)
- *G01N 27/453* (2006.01)
- *B29C 45/00* (2006.01)
- *B29C 33/40* (2006.01)

(52) U.S. Cl. .................. 204/453; 204/604; 264/328.1; 264/219

(58) Field of Classification Search ........ 204/451–455, 204/601–605; 264/299, 319, 328.1, 219
See application file for complete search history.

(56) References Cited

U.S. PATENT DOCUMENTS

| | | | |
|---|---|---|---|
| 5,707,799 A * | 1/1998 | Hansmann et al. ............. 435/6 |
| 6,270,641 B1 * | 8/2001 | Griffiths et al. ............. 204/451 |
| 6,280,589 B1 * | 8/2001 | Manz et al. .................. 204/453 |
| 6,761,962 B2 * | 7/2004 | Bentsen et al. ............. 428/188 |
| 6,800,234 B2 * | 10/2004 | Ferguson et al. ............ 264/220 |
| 6,827,831 B1 * | 12/2004 | Chow et al. ................. 204/604 |
| 2004/0046281 A1 * | 3/2004 | Kim et al. ................... 264/237 |

FOREIGN PATENT DOCUMENTS

| | | | |
|---|---|---|---|
| CA | 2310700 A1 | * | 6/2001 |
| JP | 03-191856 A | * | 8/1991 |
| JP | 11-326274 A | * | 11/1999 |
| JP | 2000-310613 | | 11/2000 |
| JP | 2001-83118 A | * | 3/2001 |
| JP | 2002-148236 A | * | 5/2002 |

OTHER PUBLICATIONS

JPO computer English language translatio of JP 2001-083118 A (Hironobu et al. ) (Mar. 30, 2001).*
JPO computer English language translation of JP 2002-148236 A (Hironobu et al.) (May 22, 2002).*
JPO computer language translation of JP 11-32674 A 9Abe Hirohisa) (Nov. 26, 1999).*
JPO English language computer translation of Kenji et al. (JP 2000-310613) (Jul. 11, 2000).*
The CAPLUS abstract of Spiro ("Hard nickel electroformed molds," Plastics (London) (1948), 12, 132-7) (publn. month unknown).*
Hirai et al. ("Nano-imprint Lithography Using Replicated Mold by Ni Electroforming," Jpn. J. Appl. Phys. vol. 41 (2002) pp. 4186-4189) Jun. 2002.*
The JPO abstract of Yokogawa (JP 03-191856 A) (Aug. 21, 1991).*

* cited by examiner

*Primary Examiner*—Alex Noguerola
(74) *Attorney, Agent, or Firm*—McGinn IP Law Group, PLLC

(57) ABSTRACT

To provide a biochip, a biochip manufacturing method, an electrophoresis method, and an electrophoresis apparatus, by which the detection accuracy may improve, there is a biochip introducing a sample in band form into a sample separation passage, by a means for reducing the band width of sample, at which the sample is before being introduced in the sample separation passage in band form. The band of sample supplied to the sample separation passage is compressed, and the expansion by diffusion may be prevented, thus the detection accuracy may improve.

15 Claims, 8 Drawing Sheets

BIOCHIP AND A MANUFACTURING METHOD OF BIOCHIP

BACKGROUND OF THE INVENTION

1. Field of the Invention

The present invention relates to a biochip, for example, a biochip in which taper sections are provided, as a means for reducing the width of band, at a sample introductory passage for introducing a sample, in order to improve the detection accuracy. Further, the present invention relates to a biochip having a simple structure so that the sample may be directly supplied into a sample separation passage without requiring the sample introductory passage. The present invention also relates to a method of manufacturing the biochip discussed as above, and relates to an electrophoresis method and an electrophoresis apparatus using such biochip.

2. Description of the Related Art

There has been provided a so-called "electrophoresis method" as a method of separating the electric charge nature matter from protein or nucleic acid. In particular, there is a known method of "capillary electrophoresis method" by using micro electrophoresis chip, in order to separate and fix a very small amount of matter. According to the "capillary electrophoresis method", a separation object maybe introduced in a separation slot by electro kinetic injection (see, for example, the Patent Document 1).

Patent Document 1: Official Gazette of Japanese Unexamined Patent Publication No. 2000-310613.

According to the Patent Document 1, first, a sample introductory passage and a sample separation passage are provided respectively. Then a small amount of reagent containing a separation object is dropped into a liquid reservoir section of the sample introductory passage. There are electrodes for electrophoresis, respectively provided at this liquid reservoir section, and at another liquid reservoir section located at the other end of the sample introductory passage. When an appropriate voltage is applied to these electrodes for electrophoresis, the sample dropped into the sample introductory passage moves to an intersection part at which the sample introductory passage perpendicularly intersects with the sample separation passage.

When the sample reaches the intersection part, an appropriate voltage is applied to other two electrodes for electrophoresis, respectively provided at other two liquid reservoir sections located at the both ends of the sample separation passage. Consequently, the sample existing only at the intersection part will be separated, and move inside the sample separation passage in the form of band, thus it is possible to carry out the optical detection at a predetermined measuring point. In this connection, the "optical detection" would mean, for example, that the optical absorbance is measured by using the UV (ultra violet) absorption property of nucleic acid molecule, or the size of nucleic acid molecule is detected by marking fluorochrome on the nucleic acid molecule so that the fluorescence may be measured.

However, the above prior art has the following disadvantages.

As discussed above, according to the prior art, the introduced sample moves to the intersection part by electrophoresis, and only the sample that reached the intersection part will then be separated and move inside the sample separation passage, and eventually will reach detecting sections respectively provided at each end of the sample separation passage. At that time, during movement of the sample, the width of the band of sample existing at the intersection part will be expanded due to molecular diffusion, thereby the detected image of electrophoresis will become unclear, which would result in a poor detection accuracy. In particular, the larger the number of base becomes (such as DNA), the lower the detection accuracy would become, and due to the difference of base number, the complete separation cannot be done.

Further, according to the prior art, the sample is first introduced from injection holes to the sample introductory passage, and then the sample is introduced to the sample separation passage being provided independently. Thus, even a sufficient volume of sample is injected from the liquid reservoir sections, the amount of sample, actually entering the sample separation passage to be used for separation, is very little, and the large amount of the sample, i.e. the remaining sample, will become useless.

In addition, as discussed above, since the two-phase electrophoresis, i.e. the introductory electrophoresis and the separation electrophoresis is required, the apparatus related to the electric power supply would become complicated.

SUMMARY OF THE INVENTION

It is an object of the present invention to provide a biochip which can improve the detection accuracy, for example by reducing the width of band introduced in the intersection part. It is another object of the present invention to provide a biochip having a simple structure and a desired detection may be carried out, without requiring the sample introductory passage. Further, it is still another object of the present invention to provide a method of manufacturing the biochip as discussed above, and to provide an electrophoresis method and an electrophoresis apparatus using such biochip.

To achieve the object mentioned above, according to claim 1 of the present invention, there is provided a biochip which introduces a sample in the form of band into a sample separation passage, characterized by a means for reducing a width of band of sample, located at a position at which the sample is before being introduced in the sample separation passage in the form of band.

According to claim 2, there is provided the biochip as claimed in claim 1, wherein the means for reducing the width of band of sample are sections in taper form, so as to reduce the width of the sample introductory passage, located at the positions at which the sample is before being introduced in the sample separation passage in the form of band.

According to claim 3, there is provided a biochip, comprising: a platy member, provided with a sample introductory passage from which a sample is introduced via injection holes, and with a sample separation passage which receives the introduced sample and discharges the sample via a discharge hole; and a seal member connected to the platy member, characterized by taper sections formed in taper form, provided in the sample introductory passage of the platy member, so that the width of the sample introductory passage is gradually reduced toward an intersection part with the sample separation passage.

According to claim 4, there is provided the biochip as claimed in claim 3, wherein at least a sample introductory passage perpendicularly intersects with at least a sample separation passage.

According to claim 5, there is provided the biochip as claimed in claim 3 or claim 4, wherein the seal member is in film form, sheet form or plate form.

According to claim 6, there is provided the biochip as claimed in any of claims 3 through 5, further comprising electrophoretic electrodes, respectively provided at positions of the injection holes and the discharge hole of the platy member, on a surface where the seal member is fixed on the platy member.

According to claim 7, there is provided the biochip as claimed in claim 6, wherein the seal member is provided with electric circuits electrically connected to the electrophoretic electrodes on a surface on the other side where the seal member is fixed on the platy member.

According to claim 8, there is provided the biochip as claimed in any of claims 3 through 7, wherein the platy member and the seal member is made of acrylic resin material or silicone resin material.

According to claim 9, there is provided the biochip as claimed in any of claims 3 through 8, wherein the platy member is provided with positioning portions for positioning of the biochip when being installed in an electrophoresis apparatus.

According to claim 10, there is provided a method of manufacturing biochip, comprising: a platy member, provided with a sample introductory passage from which a sample is introduced via injection holes, and with a sample separation passage which receives the introduced sample and discharges the sample via a discharge hole; and a seal member connected to the platy member, characterized by a step of manufacturing the platy member by thermo compression using a nickel mold.

According to claim 11, there is provided the method of manufacturing biochip as claimed in claim 10, wherein the nickel mold is manufactured by applying Ni-electroform to a master mold, formed by using a thick-film resist.

According to claim 12, there is provided the method of manufacturing biochip as claimed in claim 10 or claim 11, wherein electrophoretic electrodes and electric circuits provided on the seal member are made of platinum, gold or aluminum, formed by vacuum evaporation or sputtering.

According to claim 13, there is provided the method of manufacturing biochip as claimed in any of claims 10 through 12, wherein the platy member and the seal member are connected to each other by thermo compression or lamination.

According to claim 14, there is provided an electrophoresis apparatus, characterized by using a biochip according to any of claims 1 through 9, or by using a biochip which has been manufactured by a manufacturing method of the biochip according to any of claims 10 through 13.

According to claim 15, there is provided a biochip comprising: a platy member, without having a sample introductory passage, so as to directly receive a sample in a sample separation passage via an injection hole, and to discharge the sample via a discharge hole; and a seal member, connected to the platy member, and provided with a sample introductory nozzle at a position corresponding to the injection hole, and with another discharge hole at a position corresponding to the discharge hole of the platy member.

According to claim 16, there is provided the biochip as claimed in claim 15, wherein: the sample introductory nozzle of the seal member is in taper form so that the diameter of the sample introductory nozzle is gradually reduced in the direction of thickness of the seal member toward the platy member.

According to claim 17, there is provided the biochip as claimed in claim 15 or claim 16, wherein the seal member is in film form, sheet form or plate form.

According to claim 18, there is provided the biochip as claimed in any of claims 15 through 17, wherein the platy member further comprising electrophoretic electrodes, at the injection hole and/or the discharge hole.

According to claim 19, there is provided the biochip as claimed in claim 18, wherein, electric circuits, electrically connected to the electrophoretic electrodes, are provided on a surface of the platy member on which the platy member being fixed on the seal member.

According to claim 20, there is provided the biochip as claimed in any of claims 15 through 19, wherein the platy member and the seal member is made of acrylic resin material or silicone resin material.

According to claim 21, there is provided the biochip as claimed in any of claims 15 through 20, wherein the seal member is provided with an introductory electrode in the sample introductory nozzle, and with an electric circuit electrically connected to the introductory electrode on a surface on the other side where the seal member is fixed on the platy member.

According to claim 22, there is provided the biochip as claimed in any of claims 15 through 21, wherein the platy member is provided with positioning portions for positioning of the biochip when being installed in an electrophoresis apparatus.

According to claim 23, there is provided a method of manufacturing biochip, comprising: a platy member, without having a sample introductory passage, so as to directly receive a sample in a sample separation passage via an injection hole, and to discharge the sample via a discharge hole; and a seal member, connected to the platy member, and provided with a sample introductory nozzle at a position corresponding to the injection hole, and with another discharge hole at a position corresponding to the discharge hole of the platy member, characterized by a step of manufacturing the platy member by thermo compression using a nickel mold.

According to claim 24, there is provided the method of manufacturing biochip as claimed in claim 23, wherein the nickel mold is manufactured by applying Ni-electroform to a master mold, formed by using a thick-film resist.

According to claim 25, there is provided the method of manufacturing biochip as claimed in claims 23 or 24, wherein the seal member is manufactured, by thermo compression using nickel mold, or by injection molding, or by mechanical working, or by forming of silicone resin.

According to claim 26, there is provided the method of manufacturing biochip as claimed in any of claims 23 through 25, wherein the nickel mold is manufactured by applying Ni-forming to a master mold, which has been formed, by anisotropic etching of a silicone substrate by alkali etching solution such as potassium hydroxide (KOH), or by mechanical working using such as dicing saw.

According to claim 27, there is provided the method of manufacturing biochip as claimed in claim 25, wherein a master block for forming by silicone resin is manufactured, by anisotropic etching of a silicone substrate by alkali etching solution, or by dry etching, or by mechanical working using such as dicing saw.

According to claim 28, there is provided the method of manufacturing biochip as claimed in any of claims 23 through 27, wherein the introductory electrodes, and an electrophoretic electrode and electric circuits, provided on the platy member and the seal member, are made of platinum, gold or aluminum, formed by vacuum evaporation or sputtering.

According to claim 29, there is provided the method of manufacturing biochip as claimed in any of claims 23 through 28, wherein the platy member and the seal member are connected to each other by thermo compression or lamination.

According to claim 30, there is provided an electrophoresis method by using biochip according to any of claims 15 through 22, characterized by steps of applying a voltage to the introductory electrode of the sample introductory nozzle and the electrophoretic electrode of the platy member, so that a very little amount of the sample may be electrically dropped into the sample separation passage of the platy member.

According to claim 31, there is provided the electrophoresis method as claimed in claim 30, wherein, a very little amount of the sample dropped into the sample separation passage of the platy member is, separated, optically detected and analyzed, by a single separation electrophoresis.

According to claim 32, there is provided an electrophoresis apparatus, characterized by using a biochip according to any of claims 15 through 22, or by using a biochip which has been manufactured by a manufacturing method of the biochip according to any of claims 23 through 29, or by using an electrophoresis method according to claim 30 or claim 31.

Therefore, according to the biochip of claim 1, as for the biochip which introduces a sample in the form of band into a sample separation passage, there is provided a means for reducing a width of band of sample, located at a position at which the sample is before being introduced in the sample separation passage in the form of band, thereby it is possible to improve the detection accuracy.

For example, the means for reducing the width of band is that which reduces the width of the sample introductory passage in taper form, before the sample is introduced in the sample separation passage in the form of band. With this structure, the sample introductory passage in taper form may gather the sample in a narrow space, thereby the width of band of sample may be reduced.

According to the biochip of claim 3, there are taper sections formed in taper form, provided in the sample introductory passage of the platy member, so that the width of the sample introductory passage is gradually reduced toward an intersection part with the sample separation passage. Consequently, it is possible to gather the sample in a narrow space so as to reduce the width of band of sample supplied to the sample separation passage, and accordingly the detection accuracy may improve.

Preferably, at least a sample introductory passage perpendicularly may intersect with at least a sample separation passage.

Preferably, the seal member is in film form, sheet form or plate form.

Preferably, electrophoretic electrodes may be provided at positions of the injection holes and the discharge hole of the platy member, on a surface where the seal member is fixed on the platy member.

Preferably, the seal member may be provided with electric circuits electrically connected to the electrophoretic electrodes on a surface on the other side where the seal member is fixed on the platy member.

For example, the platy member and the seal member is made of acrylic resin material or silicone resin material.

Preferably, the platy member may be provided with positioning portions for positioning of the biochip when being installed in an electrophoresis apparatus. Consequently, the installation of the biochip into an electrophoresis apparatus may be facilitated. The positioning portion may be in the form of hole, protrusion or simple marking.

Claims 10 through 13 are those claiming the method of manufacturing biochip as discussed above.

Claim 14 is that claiming the electrophoresis apparatus, by using the biochip according to any of claims 1 through 9, or by using the biochip manufactured by the manufacturing method of the biochip according to any of claims 10 through 13.

According to the biochip of claim 15, there is provided: a platy member which receives a sample in a sample separation passage via an injection hole, and discharges the sample via a discharge hole; and a seal member, connected to the platy member, and having a sample introductory nozzle at a position corresponding to the injection hole, and with another discharge hole at a position corresponding to the discharge hole of the platy member. Thus, the sample may be directly introduced in the sample separation passage, without requiring the sample introductory passage, via the injection hole of the sample introductory nozzle provided in the seal member on the side of the platy member. Accordingly, the structure may be remarkably simplified, and in particular, since the electrophoresis only relates to the separation electrophoresis, the system including the electric power supply may be remarkably simplified.

In this case, preferably, the sample introductory nozzle may be in taper form so that the diameter of the sample introductory nozzle is gradually reduced in the direction of thickness of the seal member toward the platy member. Thus the width of band supplied to the sample separation passage may be reduced without any expansion thereof by diffusion, and it is possible to improve the detection accuracy.

Preferably, the seal member may also be in film form, sheet form or plate form.

Preferably, the platy member may further has electrophoretic electrodes, at the injection hole and/or the discharge hole.

Preferably, electric circuits, electrically connected to the electrophoretic electrodes, maybe provided on a surface of the platy member on which the platy member being fixed on the seal member.

For example, the platy member and the seal member is made of acrylic resin material or silicone resin material.

Preferably, the seal member may be provided with an introductory electrode in the sample introductory nozzle, and with an electric circuit electrically connected to the introductory electrode on a surface on the other side where the seal member is fixed on the platy member.

Preferably, the platy member as discussed above may be provided with positioning portions for positioning of the biochip when being installed in an electrophoresis apparatus. Consequently, the installation of the biochip into an electrophoresis apparatus may be facilitated. The positioning portion may be in the form of hole, protrusion or simple marking.

Claims 23 through 29 are those claiming the method of manufacturing biochip as discussed above.

According to the electrophoresis method of claim 30, the biochip according to any of claims 15 through 22 are used, by applying a voltage to the introductory electrode of the sample introductory nozzle and the electrophoretic electrode of the platy member, so that a very little amount of the sample may be electrically dropped into the sample separation passage of the platy member. Thus it is possible to supply a very little amount of sample.

Preferably, a very little amount of the sample dropped into the sample separation passage of the platy member may be separated, optically detected and analyzed, by a single separation electrophoresis.

According to the electrophoresis apparatus of claim 32, the biochip according to any of claims 15 through 22, or the biochip manufactured by the manufacturing method of the biochip according to any of claims 23 through 29, are used, or the electrophoresis method according to claim 30 or claim 31 is used.

Therefore, according to the present invention, as there is a means for reducing the width of band of sample at the position before the sample in the form of band being introduced in the sample separation passage, the width of band of sample supplied to the sample separation passage may be reduced, thereby it is possible to improve the detection accuracy.

Further, where the taper sections are formed in the sample introductory passage of the platy member, so that the width of the sample introductory passage is gradually reduced toward an intersection part with the sample separation passage, it is possible to gather the sample in a narrow space so as to reduce the width of band of sample supplied to the sample separation passage, and accordingly the detection accuracy may improve.

Further, where the positioning portions are provided, for positioning of the biochip when being installed in an electrophoresis apparatus, the installation may be facilitated.

Further, where there is provided a platy member, which receives a sample in a sample separation passage via an injection hole, and discharges the sample via a discharge hole, and where there is provided a seal member, connected to the platy member, and having a sample introductory nozzle at a position corresponding to the injection hole, and with another discharge hole at a position corresponding to the discharge hole of the platy member, thereby the sample may be directly introduced in the sample separation passage, without requiring the sample introductory passage, via the injection hole of the sample introductory nozzle provided in the seal member on the side of the platy member, such structure will have the merit in that, the structure, in particular that including the electric power supply, may be remarkably simplified.

In this case, where the sample introductory nozzle is in taper form so that the diameter of the sample introductory nozzle is gradually reduced in the direction of thickness of the seal member toward the platy member, the width of band supplied to the sample separation passage may be reduced by gathering the sample in a narrow space, thereby it is possible to improve the detection accuracy.

Further, by providing the electrophoretic electrode, it is possible to surely carry out the dropping of a very little amount of sample.

In this case, where the positioning portions are similarly provided, for positioning of the biochip when being installed in an electrophoresis apparatus, the installation may also be facilitated.

BRIEF DESCRIPTION OF THE DRAWINGS

The invention will be described below in detail with reference to the accompanying drawings, in which:

FIGS. 5(*a*) and (*b*) are views for explaining the effect of the first embodiment of the present invention, in which FIG. 5(*a*) is a plan view showing a state of band according to the first embodiment, and FIG. 5(*b*) is a plan view showing a state of band according to a prior art;

DETAILED DESCRIPTION OF THE INVENTION

First Embodiment

Figure 1:
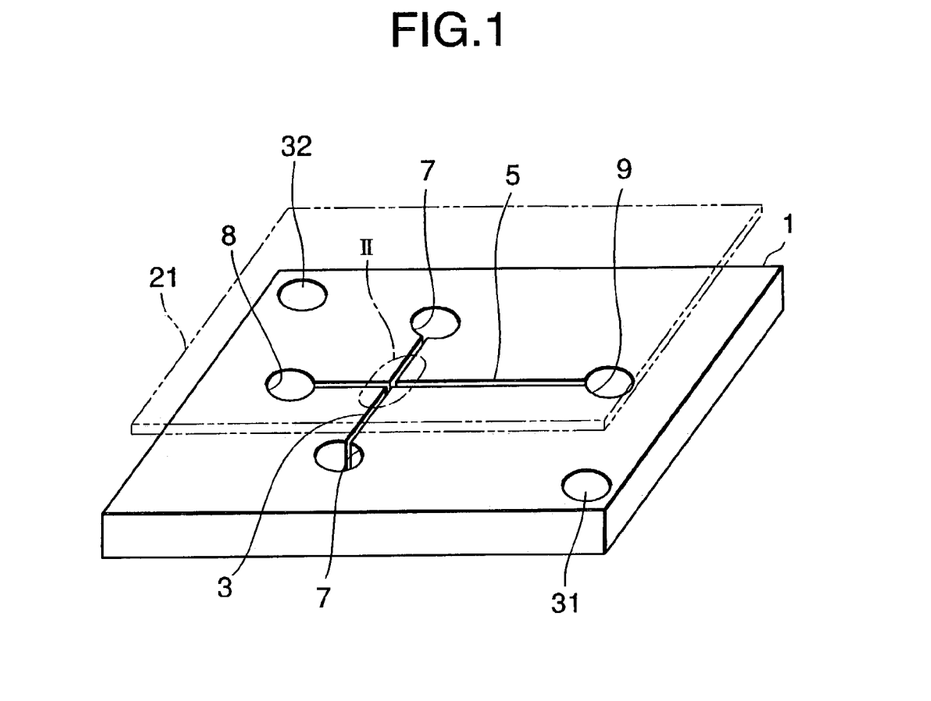
FIG. 1 is a perspective view of a platy member used for a biochip according to a first embodiment of the present invention.

A first embodiment of the present invention will now be described with reference to FIGS. 1 through 5. FIG. 1 is a perspective view showing a structure of a platy member 1 used for a biochip according to the first embodiment. The platy member 1 comprises a slot-shape of sample introductory passage 3 and also a slot-shape of sample separation passage 5, crossing to each other in a perpendicular direction. There are penetrating injection holes 7, 7 respectively provided at the both ends of the sample introductory passage 3. There is also a penetrating injection hole 8 and a penetrating discharge hole 9, respectively provided at the both ends of the sample separation passage 5.

The platy member 1 is made of transparent or semi-transparent material, so that the optical detection by UV absorption or fluorescence measurement can be carried out. The platy member is preferably made of synthetic resin, because of their good electric insulation property, reproducibility, and production efficiency. For example, the platy member 1 may be made of acrylic resin such as polymethyl methacrylate. Further, by considering the disposable use, the platy member 1 is preferably made of biodegradable plastic.

The platy member 1 may also be made of e.g. silicone resin, other than acrylic resin as discussed above.

The size of the platy member 1 should be minimized for the purpose of downsizing of the electrophoresis apparatus, and at the same time, should be determined by taking account of the good operativity. Thus, the size may be the square of e.g. 30 mm to 50 mm. The thickness of the platy member 1 is preferably about 1 mm–2 mm, by taking account of good molding productivity and good operativity.

The platy member 1 may be manufactured by molding, by taking account of good production efficiency and reproducibility.

The injection holes 7, 7, the injection hole 8, and the discharge hole 9, respectively provided in the platy member 1, serve as liquid reservoir sections for injecting and discharging the sample. The diameter of the inner periphery of each hole is preferably 1 mm–5 mm, by taking account of good operativity for the injection of sample.

The sample introductory passage 3 and the sample separation passage 5 respectively serve to the introduction and separation of sample. According to the present embodiment, since the sample introductory passage 3 and the sample separation passage 5 are independently provided, the volume of sample introduced in the sample separation passage 5 may be controlled, thereby it is possible to improve the detection accuracy.

Figure 2:
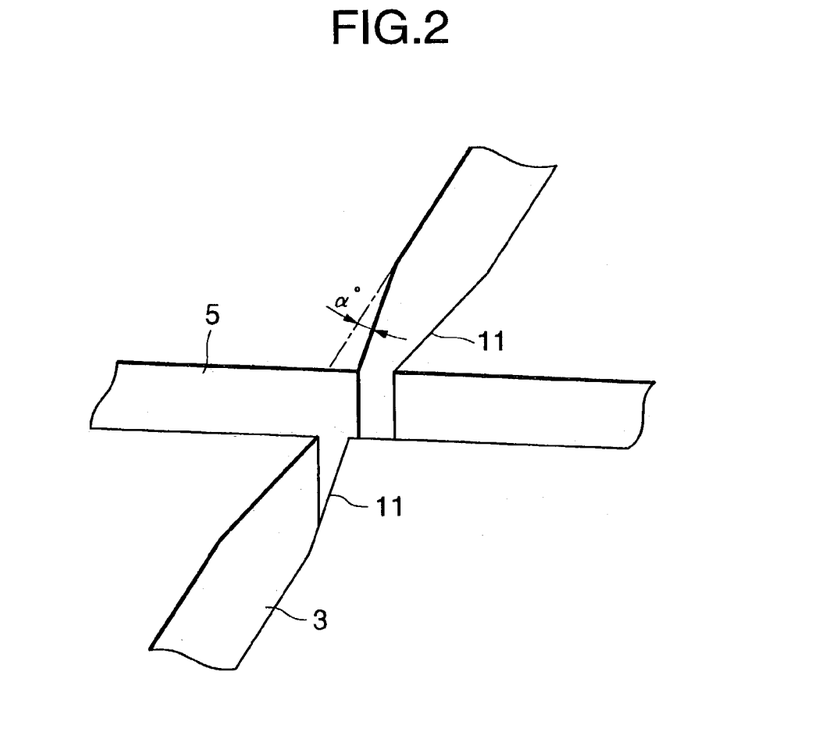
FIG. 2 is an enlarged perspective view showing a part II of FIG. 1 according to the first embodiment of the present invention.

As illustrated in FIG. 2, there are taper sections 11, 11 in the sample introductory passage 3, as a means for reducing the width of band of sample. The width of the sample introductory passage 3 becomes gradually narrower at the taper section 11, in the direction of an intersection part with the sample separation passage 5. The taper angle of this section is indicated as ($\alpha°$) in FIG. 2. With this structure, as the opening area through which the sample passes becomes narrower, the moving sample will be collected in the narrow area. Consequently, the width of band of sample, moving from the sample introductory passage 3 to the sample separation passage 5, may become narrower, thus it is possible to improve the detection accuracy.

The width of the sample separation passage 5 is preferably 30 µm–100 µm, and the depth thereof is preferably 10 µm–100 µm, by taking account of the down-sizing, good operativity, good molding productivity and preciseness of the electrophoresis apparatus. The length of the sample separation passage 5 is preferably 10 mm–50 mm.

The platy member 1 is manufactured by a method as discussed below.

First, a photomask of pattern of forms, corresponding to the sample introductory passage 3, the sample separation passage 5, the injection holes 7, 7, the injection holes 8 and the discharge holes 9, is prepared, and the patterning of a super-thick film resist is carried out by using this photomask. The thus obtained super-thick film resist serves as a master mold, from which a mold is prepared by Ni-electroform. The mold is then used for the molding of platy member 1 as illustrated in FIG. 1 by thermo compression, made of PMMA (polymethyl methacrylate).

The platy member 1 is provided with positioning holes 31, 32.

Figure 3:
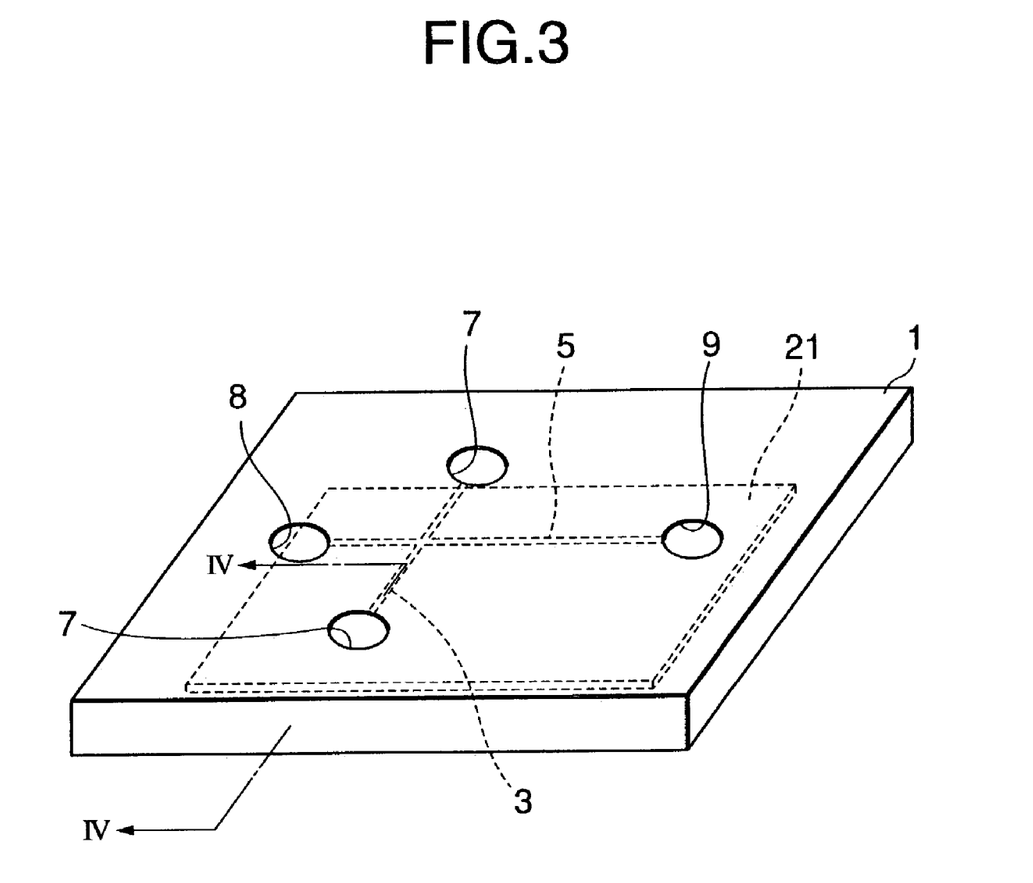
FIG. 3 is a perspective view showing a structure of assembled biochip according to the first embodiment of the present invention.
Figure 4:
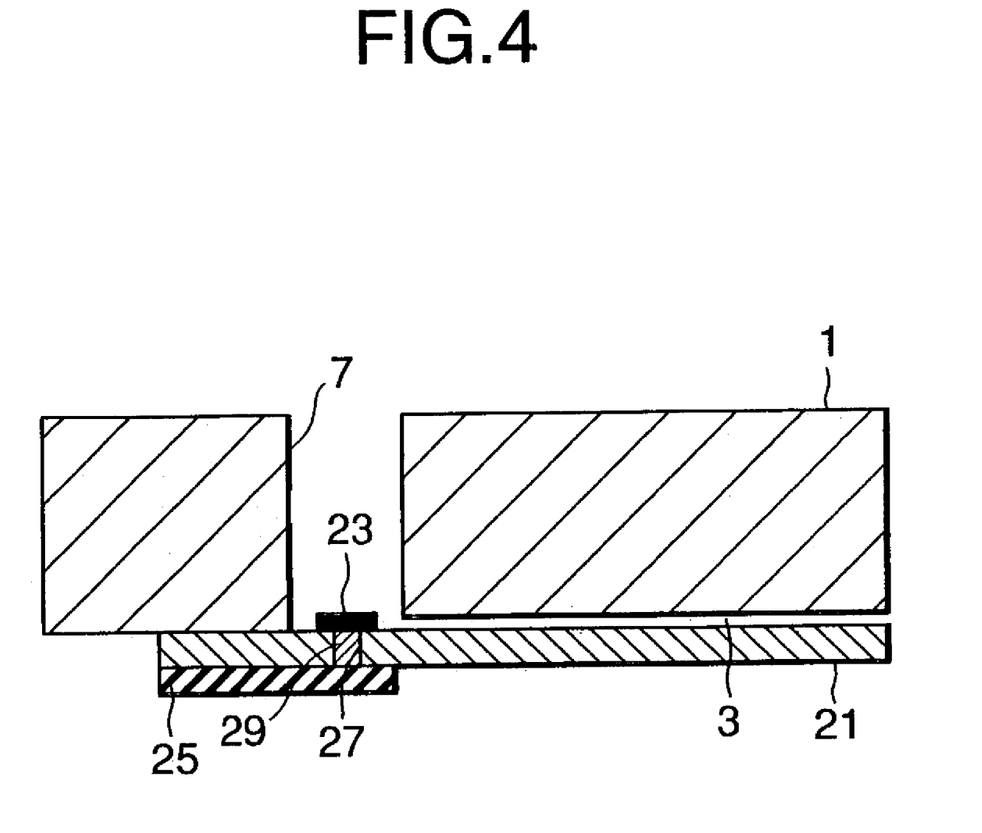
FIG. 4 is a sectional view according to the first embodiment of the present invention, as viewed from the line IV—IV of FIG. 3.

There is a seal member 21, as illustrated by imaginary line in FIG. 1, fixed on the upper surface of the platy member 1 as discussed above. FIG. 3 shows the state, in which the seal member 21 is fixed on the platy member 1, and thereafter the platy member 1 is reversed upside down. FIG. 4 is a partial sectional view showing the structure according to the state of FIG. 3. The seal member 21 is smaller than the platy member 1 by a predetermined size, so that the above discussed positioning holes 31, 32 may not be concealed.

When the platy member 1 serves as a biochip to be installed in an electrophoresis apparatus, the platy member 1 will be used in a state as shown in FIG. 3.

As illustrated in FIG. 4, there is an electrophoretic electrode 23, provided on the surface of the seal member 21 being fixed on the platy member 1, at the position corresponding to the injection hole 7 of the platy member 1. There is also an electric circuit 23, provided on the other side of the fixed surface of the seal member 21, electrically connected to the electrophoretic electrode 23. Accordingly, the seal member 21 has a penetrated hole 27 at the position corresponding to the injection hole 7 of the platy member 1. The inner peripheral surface of the penetrated hole 27 is coated by silver paste 29, thereby the penetrated hole 27 serves as a conductive through-hole. Thus, the electrophoretic electrode 23 is provided at the end of the penetrated hole 27 on the side that the seal member 21 is fixed on the platy member 1, and the electric circuit 25, e.g. made of aluminum, is provided on the other end of the penetrated hole 27 on the other side of the seal member 21.

The electrophoretic electrode 23 and the electric circuit 25 may be formed, for example, by plating, vapor deposition or printing. Among these forming methods, the plating would rather be problematic, as for durability of the used material against plating. Thus, it is preferable to be formed by printing or vapor deposition, from the viewpoint of the productivity. In particular, it is preferable to use vacuum evaporation or sputtering. Although the electrophoretic electrode 23 will show the sufficient performance as long as it is made of metal or conductive material, from the viewpoint that the corrosion of the electrophoretic electrode 23 would give a bad effect to the electrophoretic condition, it is preferable to be made of any material having excellent corrosion resistance, such as gold, platinum, carbon, etc. The electric circuit 25 is preferably made of platinum, copper or aluminum, by taking account of the price and general availability. The form of the electrophoretic electrode 23 is not limited as long as the conduction is secured, but the preferable thickness is, for example, 0.01 µm–0.05 µm, and he preferable width is, for example, 1 mm–5 mm.

Although FIG. 4 illustrates the injection hole 7 and the peripheral structure on one side, the other injection hole 7 on the other side, as well as the injection hole 8 and the discharge hole 9 have the substantially same structure. That is, each hole has an electrophoretic electrode 23 and the electric circuit 25 on the seal member 21. Thus, when an appropriate voltage is applied to a pair of electrophoretic electrodes 23, 23, provided at the position of a pair of injection holes 7, 7, the electrophoresis is carried out, thereby the sample introduced in the sample introductory passage 3 is moved to the sample separation passage 5. Thereafter, when an appropriate voltage is applied to a pair of electrophoretic electrodes 23, 23 respectively provided at the position of the injection hole 8 and the discharge hole 9, the electrophoresis is further carried out, thereby the band of sample introduced in the sample separation passage is moved accordingly.

The seal member 21, having the structure as discussed above, is fixed on the platy member 1, thus the biochip as illustrated in FIGS. 1 and 3 is provided.

The seal member 21 may be fixed on the platy member 1, by means of mechanical compression, adhesive, thermo compression, thermo welding, lamination, etc.

The seal member 21 is preferably made of transparent or semi-transparent material likewise the case of the platy member 1 as discussed above, by taking account of carrying out the detection by UV absorption fluorescence measurement. The material of the seal member 21 is preferably a synthetic resin, which may be formed into a shape of film to be easily adhered to the surface of the platy member 1, or which may be formed into a shape of sheet having the good adherent performance. In particular, an acrylic resin such as polymethyl methacrylate may be preferably used for the seal member 21, by taking account of the productivity. It is also preferable to use a silicone resin material because of the good adherent performance. Further, likewise the case of the platy member 1, by taking account of the disposable use, the seal member 21 is also preferably made of biodegradable plastic.

The biochip as discussed above is installed in an unillustrated electrophoresis apparatus. The electrophoresis apparatus is provided with a means for illuminating the sample, and which is preferably provided with a light source and a light condensing means. The light source is preferably a mercury lamp, light emitting diode (LED), laser lamp, etc. The light condensing means is preferably an optical fiber, dichroic mirror, object lens, and other lens such as optical filter. The combination of these light condensing means is also preferable. There is also a means, for measuring the detected light from the sample, which is at least provided with an optical sensor. Thus, means for measuring the light is preferably provided with a fluorescent sensor, photomultiplier, charge coupled device (CCD), photodiode, etc.

The function of the biochip according to the present embodiment will now be described, based on the structure as discussed above.

First, a separation medium is filled in the injection holes 7, 7, the injection hole 8 and the discharge hole 9, as well as in the every passage. The separation medium may be filled, by means of e.g. capillary phenomenon, compression by using a syringe, or decompression injection by using a vacuum pump.

Then, the sample is dropped into one of the injection hole 7, and an appropriate voltage is applied to the pair of electrophoretic electrodes 23, 23 respectively provided at the pair of injection holes 7, 7. Consequently, the electrophoresis is carried out, and the sample dropped into the one of the injection hole 7 moves inside the sample introductory passage 3 toward the sample separation passage 5.

When the sample moves inside the sample introductory passage 3, the taper section 11 serves to gather the coming sample to a narrow space. Consequently, the width of band of sample, supplied to the intersection part with the sample separation passage 5, becomes narrower, thus the narrow band of sample will be supplied to the intersection part. Then an appropriate voltage is applied to the pair of electrophoretic electrodes 23, 23 respectively provided at the injection hole 8 and the discharge hole 9, and the electrophoresis is further carried out. Accordingly, the band of sample, supplied to the intersection part, intermittently moves inside the sample separation passage 5.

In this state, the sample is illuminated at a predetermined timing, thereby the detected light from the sample may be measured. Thus a desired detection may be carried out.

The present embodiment has the following merits.

First, as the taper section 11 is provided at a portion of the sample introductory passage 3, the sample moving toward the sample separation passage 5 may be gathered to a narrow space, thereby it is possible to reduce the width of band supplied to the sample separation passage 5. Thus, the it is possible to improve the detection accuracy.

Figure 5A:
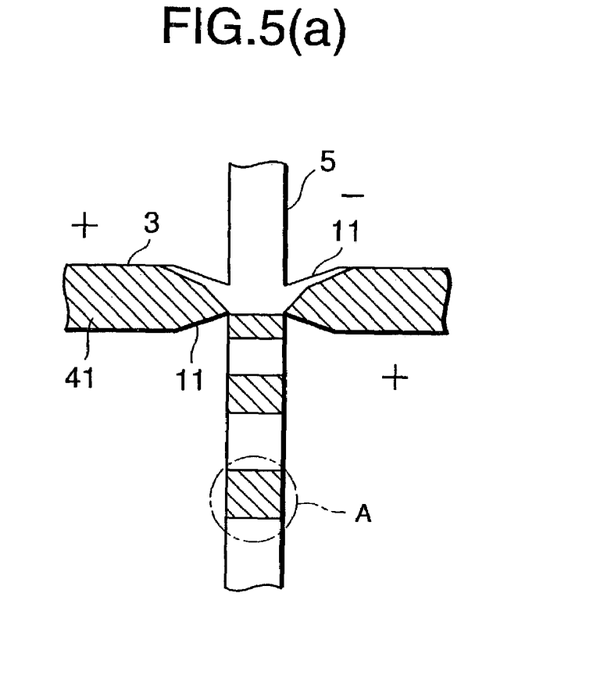
Figure 5B:
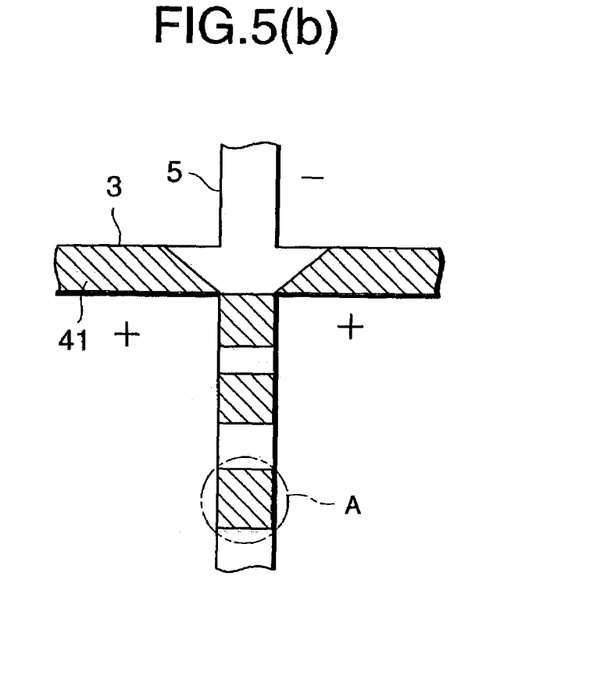

This effect may be confirmed with reference to FIG. 5. FIG. 5(a) shows the state according to the present embodiment, and FIG. 5(b) shows the state according to a prior art having no taper section 11. According to the present embodiment as illustrated in FIG. 5(a), the taper section 11 gathers the coming sample to a narrow space, thereby it is possible to reduce the width of band of sample 41, which is then supplied to the sample separation passage 5. On the other hand, according to the prior art as illustrated in FIG. 5(b), as there is no such effect, the band inside the sample separation passage 5 has the wider width.

FIG. 5(a) (as well as FIG. 5(b)) illustrates a portion A, surrounded by a circle of chain line, showing a detecting position A. When the state of the band at the detecting position A of FIG. 5(a) is compared with that of FIG. 5(b), as discussed above, according to the prior art shown in FIG. 5(b), the width of band becomes wider, and on the other hand, according to the present embodiment shown in FIG. 5(a), the width of band becomes narrower.

As the platy member 1 is provided with the positioning holes 31, 32 used for the installment in the electrophoresis apparatus, the biochip may be installed in the electrophoresis apparatus easily.

Second Embodiment

Figure 6:
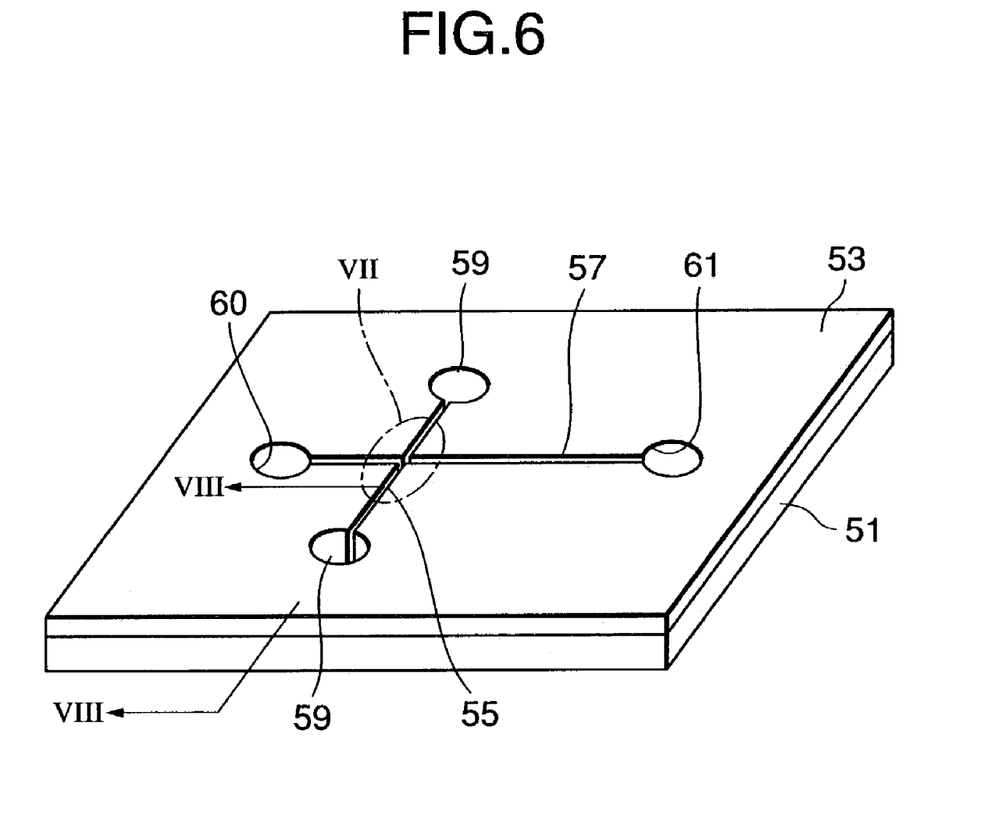
FIG. 6 is a perspective view of a glass platy member used for a biochip according to a second embodiment of the present invention.

A second embodiment of the present invention will now be described with reference to FIGS. 6 through 8. There is a platy member 51 as illustrated in FIG. 6. The platy member 51 is made of e.g. glass or acrylic material, and a thick-film resist 53 is provided on one side of the platy member 51. The thick-film resist 53 is provided with a sample introductory passage 55 and a sample separation passage 57 crossing at an intersection part with each other. Both ends of the sample introductory passage 55 are respectively provided with penetrating injection holes 59, 59, and both ends of the sample separation passage 57 are respectively provided with an penetrating injection hole 60 and a penetrating discharge hole 61.

As illustrated in FIG. 6, a seal member 62 is fixed on the side of the thick-film resist 53 of the platy member 51 as discussed above. The seal member 62 has, injection holes 64, 64, another unillustrated injection hole, and a discharge hole, corresponding to the positions of injection holes 59, 59, an injection hole 60, and a discharge hole 61 formed on the side of the platy member 51. Further, as illustrated in FIG. 8, there is an electrophoretic electrode 65 provided in the injection hole 59 on the side of the platy member 51, and there is an electric circuit 67 provided at the position between the seal member 62 and the thick film resist 53. The electric circuit 67 and the electrophoretic electrode 65 are electrically connected.

Figure 8:
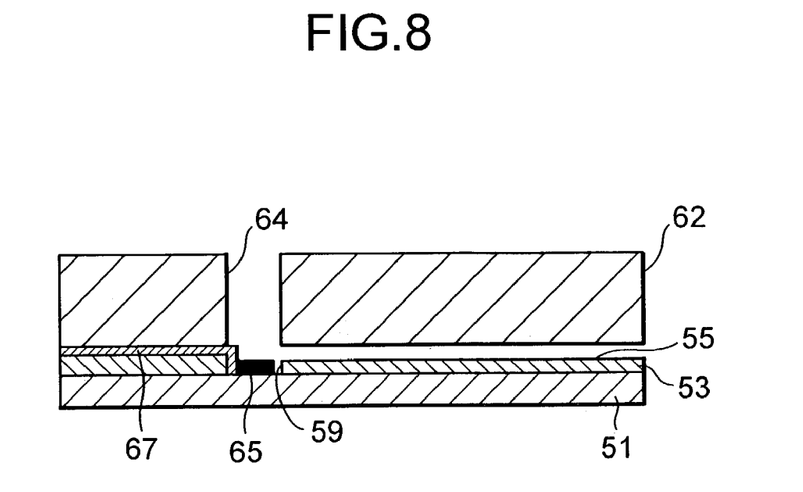
FIG. 8 is a sectional view according to the second embodiment of the present invention, as viewed from the line VIII—VIII of FIG. 6.

Although FIG. 8 illustrates one of the injection holes 59, 59 and the peripheral structure thereof, there is also the electrophoretic electrode 65 and the electric circuit 67, provided at the other injection hole 59, the injection hole 60 and the discharge hole 61.

Figure 7:
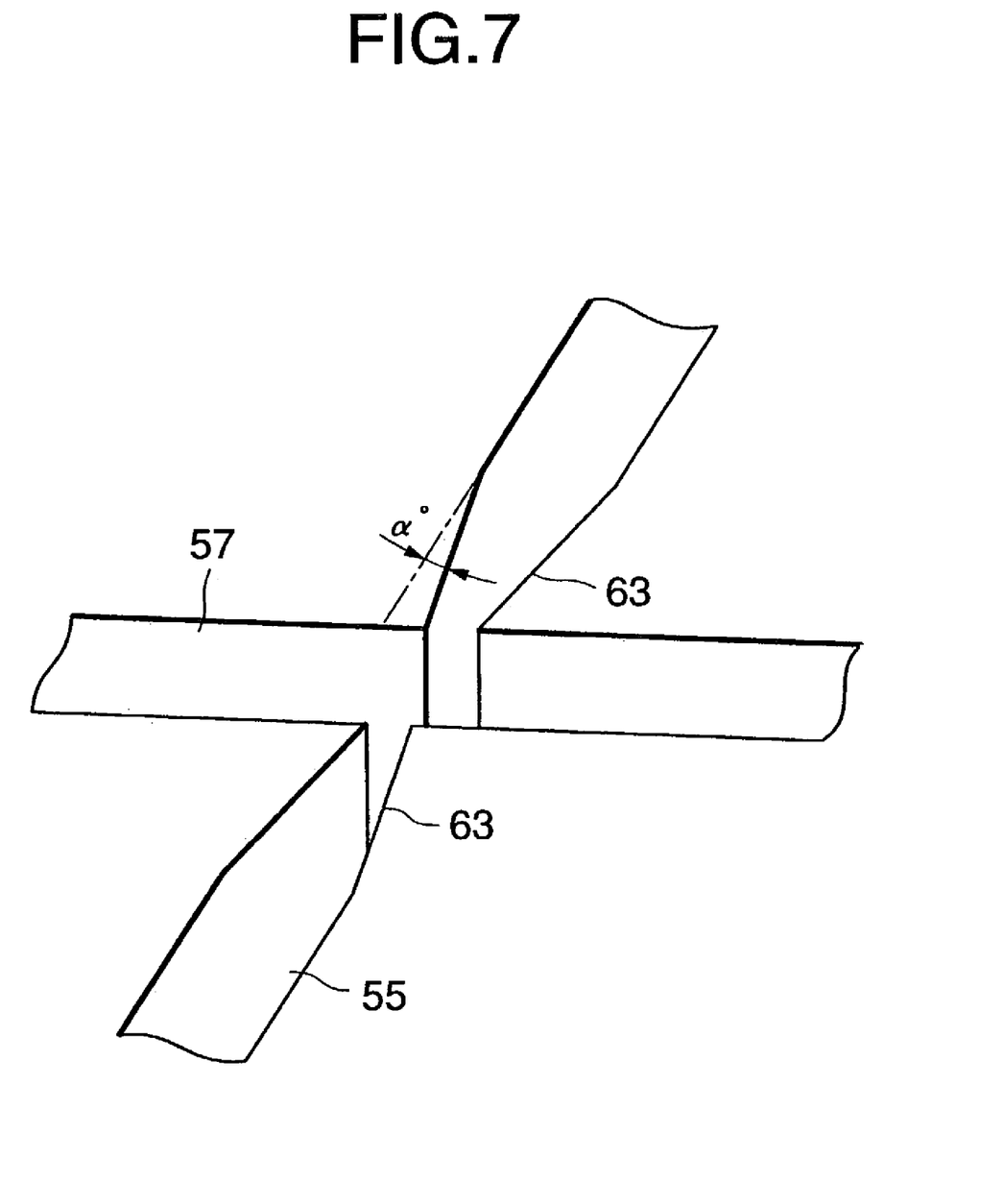
FIG. 7 is an enlarged perspective view showing a part VII of FIG. 6 according to the second embodiment of the present invention.

As illustrated in FIG. 7 the sample introductory passage 55 as discussed above is provided with taper sections 63, 63, likewise the case of the first embodiment.

Consequently, according to the second embodiment, it is possible to obtain the same function as that of the first embodiment.

Third Embodiment

A third embodiment of the present invention will now be described with reference to FIGS. 9 through 12. According to the first and second embodiments, the sample is first supplied to the sample introductory passage, and then the sample is supplied to the sample separation passage. According to the third embodiment, however, there is no sample introductory passage, so that the sample may be supplied to the sample separation passage directly.

Figure 9:
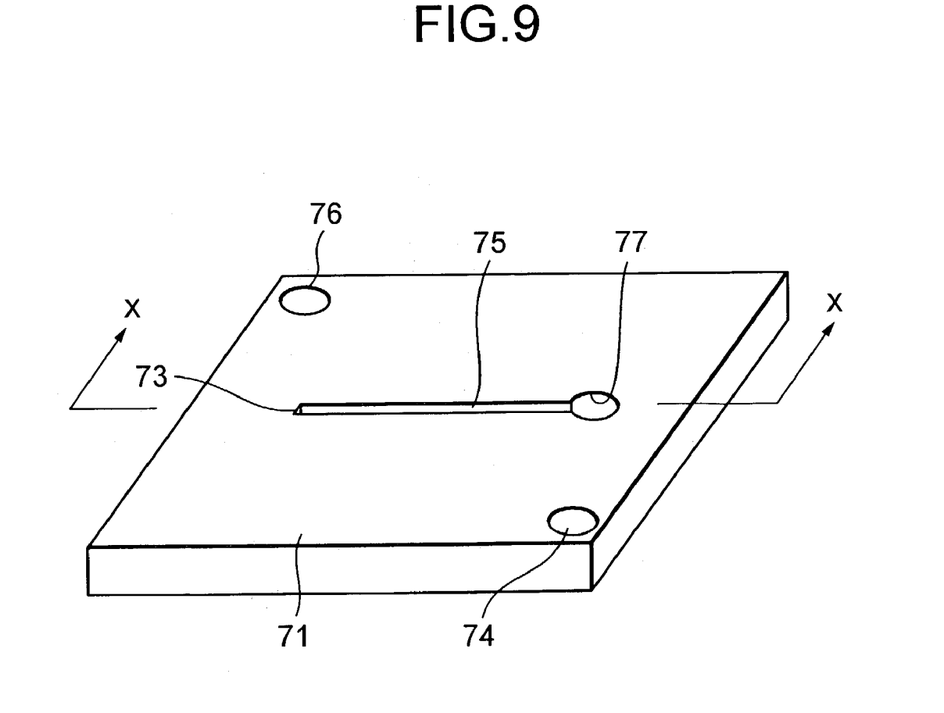
FIG. 9 is a perspective view of a platy member used for a biochip according to a third embodiment of the present invention.
Figure 10:
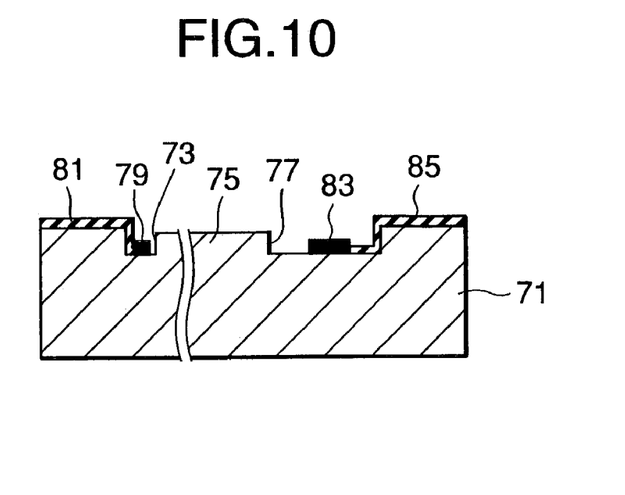
FIG. 10 is a sectional view according to the third embodiment of the present invention, as viewed from the line X—X of FIG. 9.

There is a platy member 71 as shown in FIG. 9. The platy member 71 is provided with a sample drop portion 73 and a sample separation passage 75. There is a discharge hole 77 provided at one end of the sample separation passage 75. As illustrated in FIG. 10, there is an electrophoretic electrode 79, provided at the sample drop portion 73 of the platy member 71, and electrically connected to an electric circuit 81 elongating to the outside of the sample drop portion 73. Similarly, there is an electrophoretic electrode 83 and an electric circuit 85 on the side of the discharge hole 77. The platy member 71 has positioning holes 74, 76.

Figure 11:
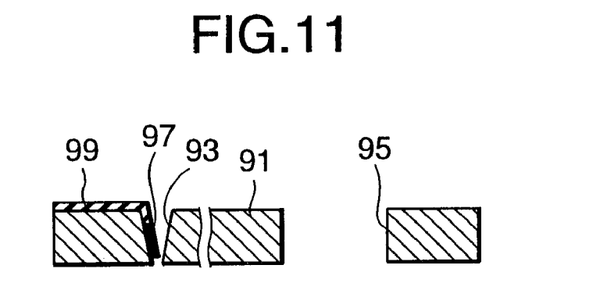
FIG. 11 is a sectional view showing a seal member used for the biochip according to the third embodiment of the present invention.

There is a seal member 91 having the structure as illustrated in FIG. 11. The seal member 91 has a sample introductory nozzle 93 formed at the position corresponding to the sample drop portion 73 of the platy member 71. The seal member also has a penetrating discharge hole 95 at the position corresponding to the discharge hole 77 of the platy member 71. The sample introductory nozzle 93 is in taper form, so that the diameter thereof may be gradually reduced in the direction of the thickness of the seal member 91 (i.e. in the downward direction). There is a sample introductory electrode 97, provided in the sample introductory nozzle 93, and electrically connected to an electric circuit 99 elongating to the outside of the sample introductory nozzle 93.

The platy member 71 may be manufactured, for example by thermo compression using a nickel mold. At that time, the nickel mold may be manufactured by applying Ni-electroform to a master mold, which has been formed by using a thick-film resist.

The seal member 91 may be manufactured, for example by thermo compression for which a nickel mold is used, or by injection molding, by mechanical working, or by silicone resin forming. For that purpose, the nickel mold is manufactured by applying Ni-forming to a master mold, which has been formed, by anisotropic etching of a silicone substrate for which alkali etching solution such as potassium hydroxide (KOH) has been used, or by mechanical working for which a dicing saw, etc. has been used. Further, a master block for forming by silicone resin is manufactured, by anisotropic etching of a silicone substrate for which alkali etching solution has been used, or by dry etching, or by mechanical working for which a dicing saw, etc. has been used.

Figure 12:
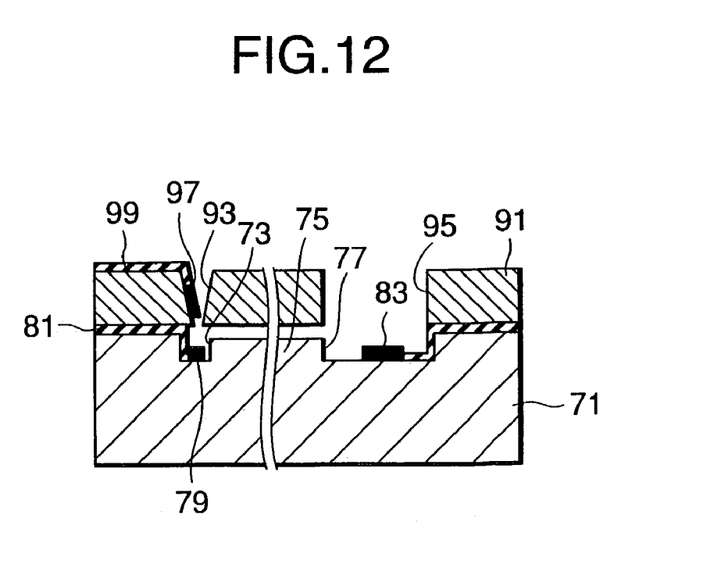
FIG. 12 is a sectional view showing the structure of the biochip according to the third embodiment of the present invention.

Thus, the biochip as illustrated in FIG. 12 may be obtained by fixing the seal member 91 having the above structure on the platy member 71.

The function of the biochip according to the third embodiment will now be described, based on the structure as discussed above.

First, a separation medium is filled in the sample separation passage 75 and the discharge hole 77, from the discharge hole 77.

Then, the sample is dropped from the sample introductory nozzle 93. As the sample introductory nozzle 93 is in taper form, the dropped sample is gathered to a narrow space. At that time, an appropriate voltage is applied to the sample introductory electrode 97 and the electrophoretic electrode 79, so that the electric effect may secure the movement of the dropped sample.

Then an appropriate voltage is applied to the pair of electrophoretic electrodes 79, 83, thereby the electrophoresis is carried out, and the dropped sample intermittently moves inside the sample separation passage 75. In this state, the sample is illuminated at a predetermined timing, thereby the detected light from the sample may be measured. Thus a desired detection may be carried out.

Thus, according to the third embodiment, the sample introductory passage as described in the first and second embodiments is not required, so the simple structure of the biochip may be realized.

Further, since the sample introductory nozzle 93 is in taper form, in which the diameter thereof is gradually reduced in the downward direction, the sample is gathered in a narrow space, thereby the width of band supplied to the sample separation passage 75 may be reduced. Consequently, it is possible to improve the detection accuracy.

In addition, according to the electric effect between the sample introductory electrode 97 and the electrophoretic electrode 79, it is possible to surely drop a very small amount of sample.

The present invention is not limited to the first through third embodiments as described above.

For example, according to the first embodiment, the taper section 11 is provided at the position before the intersection part of the sample introductory passage 3 with the sample separation passage 5. However, the position of the taper section 11 may be determined arbitrarily. It is also possible to form the sample introductory passage 3 in a taper shape as a whole.

According to the third embodiment, although the sample introductory nozzle 93 is in the taper shape as a whole, it is also possible to provide a taper section at a part of the sample introductory nozzle 93.

Further, it is also possible to provide positioning protrusions instead of the positioning holes, or to provide simple markings.

What is claimed is:

1. A biochip comprising:
   a platy member, by which a sample is directly received inside a sample separation passage via injection holes without requiring a sample introductory passage, and comprising a discharge hole; and
   a seal member connected to said platy member, comprising a sample introductory nozzle at a position corresponding to said injection hole, and another discharge hole at a position corresponding to said discharge hole of said plaly member,
   wherein said seal member comprises an introductory electrode in said sample introductory nozzle, and electric circuits electrically connected to said introductory electrode on a surface of another side of said seal member from a side where said seal member is fixed on said platy member,
   wherein said platy member comprises electrophoretic electrodes, respectively provided at positions of said injection hole and said discharge hole of said platy member,
   wherein when a voltage is applied to said introductory electrode and said electrophoretic electrode of said injection hole of said plaly member, a small amount of said sample may be electrically dropped into said sample separation passage of said platy member.

2. The biochip as claimed in claim 1, wherein:
   at least a sample introductory passage perpendicularly intersects with at least said sample separation passage.

3. The biochip as claimed in claim 1, wherein:
   said seal member comprises one of a film, a sheet and plate.

4. The biochip as claimed in claim 1, wherein:
   said platy member and said seal member comprise at least one of an acrylic resin material and a silicone resin material.

5. The biochip as claimed in claim 1, wherein:
   said platy member comprises positioning portions for positioning of said biochip when being installed in an electrophoresis apparatus.

6. An electrophoresis apparatus, comprising a biochip according to claim 1.

7. A method of manufacturing a biochip, comprising:
   a platy member, comprising:
      a sample introductory passage from which a sample is introduced via injection holes; and
      a sample separation passage which receives said introduced sample and discharges said sample via a discharge hole; and
   a seal member connected to said platy member, said seal member comprising taper sections formed in taper form, provided in said sample introductory passage of said platy member, so that a width of said sample introductory passage is gradually reduced toward an intersection part with said sample separation passage, said method comprising:
      manufacturing said platy member by thermo compression using a nickel mold.

8. The method of manufacturing a biochip as claimed in claim 7, wherein:
   said nickel mold is manufactured by applying Nielectroform to a master mold, formed by using a thick-film resist.

9. The method of manufacturing a biochip as claimed in claim 7, wherein:
   electrophoretic electrodes and electric circuits provided on said seal member comprise at least one of platinum, gold and aluminum, formed by one of vacuum evaporation and sputtering.

10. The method of manufacturing a biochip as claimed in claim 7, wherein:
    said platy member and said seal member are connected to each other by one of thermo compression and lamination.

11. An electrophoresis apparatus, comprising a biochip which has been manufactured by a manufacturing method of said biochip according to claim 7.

12. The biochip as claimed in claim 7, wherein said sample introductory passage and said sample separation passage are independently provided.

13. The biochip as claimed in claim 7, wherein said taper sections are disposed at a point of intersection of said sample separation passage and said sample introductory passage.

14. An electrophoresis method of using a biochip, comprising:
    a platy member, devoid of a sample introductory passage, so as to directly receive a sample in a sample separation passage via an injection hole, and to discharge said sample via a discharge hole; and
    a seal member, connected to said platy member, comprising:
       a sample introductory nozzle at a position corresponding to said injection hole; and
       another discharge hole at a position corresponding to said discharge hole of said platy member, said method comprising:
          applying a voltage to an introductory electrode of said sample introductory nozzle and an electrophoretic electrode of said platy member, so that a very little amount of said sample may be electrically dropped into said sample separation passage of said platy member.

15. The electrophoresis method as claimed in claim 14, wherein:
    said very little amount of said sample dropped into said sample separation passage of said platy member is separated, optically detected, and analyzed by a single separation electrophoresis.

* * * * *